(12) United States Patent
Tanoue et al.

(10) Patent No.: US 9,700,692 B2
(45) Date of Patent: Jul. 11, 2017

(54) VOICE ASSIST APPARATUS

(71) Applicant: UEMURA ENTERPRISE CO. LTD, Kumamoto (JP)

(72) Inventors: Hirotoshi Tanoue, Kumamoto (JP); Masaaki Iwashita, Kumamoto (JP); Takashi Funasaki, Kumamoto (JP); Jun Shimizu, Kumamoto (JP); Fusao Jou, Kumamoto (JP); Shingo Yamashita, Kumamoto (JP); Yukihiro Uemura, Kumamoto (JP)

(73) Assignee: UEMURA ENTERPRISE CO. LTD, Kikuchigun (JP)

( * ) Notice: Subject to any disclaimer, the term of this patent is extended or adjusted under 35 U.S.C. 154(b) by 284 days.

(21) Appl. No.: 14/600,242

(22) Filed: Jan. 20, 2015

(65) Prior Publication Data
US 2016/0038702 A1 Feb. 11, 2016

(30) Foreign Application Priority Data
Aug. 8, 2014 (JP) ................... 2014-004228

(51) Int. Cl.
*A61M 16/00* (2006.01)
*A61M 16/04* (2006.01)
(Continued)

(52) U.S. Cl.
CPC ........ *A61M 16/0468* (2013.01); *A61M 16/00* (2013.01); *A61M 16/0434* (2013.01);
(Continued)

(58) Field of Classification Search
CPC .......... A61M 16/0468; A61M 16/0434; A61M 16/00; A61M 16/206; A61M 16/20;
(Continued)

(56) References Cited

U.S. PATENT DOCUMENTS 3,747,127 A * 7/1973 Taub ................. A61M 16/0468
623/9
4,274,162 A * 6/1981 Joy ......................... A61F 2/203
623/9

(Continued)

FOREIGN PATENT DOCUMENTS

JP 2009-153775 7/2009

*Primary Examiner* — Steven Douglas
(74) *Attorney, Agent, or Firm* — Lex IP Meister, PLLC

(57) ABSTRACT

The present invention provides a voice assist apparatus capable of vocalization in a near-natural voice by correctly flowing and blocking voice assist gas during expiration and inspiration, respectively, of a patient even when the pressure inside the operation tube relatively slightly increases and decreases. In the voice assist apparatus, the main body has a first chamber connected with a second end of the voice assist gas-inlet tube, a second chamber connected with a second end of the voice assist tube, a third chamber connected with a second end of the operation tube, a dividing wall dividing between the first chamber and the second chamber except an opening communicating the first chamber with the second chamber, and a membrane formed elastically deformably to open and close the opening and isolates the third chamber from the first chamber and the second chamber.

2 Claims, 3 Drawing Sheets

(51) Int. Cl.
*A61M 16/20* (2006.01)
*A61F 2/20* (2006.01)

(52) U.S. Cl.
CPC .......... *A61M 16/20* (2013.01); *A61M 16/206* (2014.02); *A61F 2002/206* (2013.01); *A61M 16/202* (2014.02); *A61M 16/209* (2014.02); *A61M 2205/07* (2013.01); *A61M 2205/52* (2013.01)

(58) Field of Classification Search
CPC .......... A61M 2205/52; A61M 2205/07; A61M 16/202; A61M 16/209; A61F 2002/206
See application file for complete search history.

(56) References Cited

U.S. PATENT DOCUMENTS

| | | | | |
|---|---|---|---|---|
| 4,494,252 | A * | 1/1985 | Chaoui | A61F 2/203 128/207.16 |
| 2004/0187941 | A1* | 9/2004 | Seder | A61F 2/203 137/855 |
| 2012/0145156 | A1* | 6/2012 | Lofaso | A61M 16/206 128/205.24 |
| 2015/0034089 | A1* | 2/2015 | Donlon | A61M 16/0468 128/207.15 |

* cited by examiner

VOICE ASSIST APPARATUS

RELATED APPLICATIONS

This application claims priority to Japan Utility Model Application No. 2014-004228 filed on Aug. 8, 2014, and all the benefits accruing therefrom under 35 U.S.C. §119, the content of which in its entirety is herein incorporated by reference.

BACKGROUND

1. Field

The present invention relates to a voice assist apparatus. More specifically, the present invention relates to a voice assist apparatus used with an artificial respiratory device provided with an inspiration gas-inlet tube, an endotracheal tube, and a pressure on-off valve, the pressure on-off valve being connected with the inspiration gas-inlet tube and a first end of the endotracheal tube, the pressure on-off valve being opened up to and closed off from atmosphere at the timings of expiration and inspiration, respectively, of a patient.

2. Description of the Related Art

Conventionally, patients who use an artificial respirator connected with an endotracheal tube endotracheally inserted from an incision in their trachea under their vocal chords breathe with the artificial respiratory device. In this case, since expired air from their lungs during expiration tends to flow to the endotracheal tube, the expired air to flow to their vocal chords is reduced so as to insufficiently vibrate their vocal chords. Therefore, patients who use an artificial respirator hardly vocalize.

Accordingly, a voice assist apparatus include an artificial respiratory device provided with a gas feeder supplying inspiration gas for a patient, an endotracheal tube endotracheally inserted from the trachea incision of a patient, a respiratory tube communicating the gas feeder with the endotracheal tube, and an on-off valve divergingly communicating the respiratory tube with atmosphere; and a vocalization device provided with a voice assist tube with a first end being endotracheally inserted from the trachea incision of a patient, an inlet tube communicating the first end with a supply source of voice assist gas, an on-off valve operated by pressure inside the tubes communicated therewith, the on-off valve communicating the inlet tube with the voice assist tube, and an operation tube connected with the on-off valve to operate the on-off valve, in which the operation tube communicates with the respiratory tube at its middle, and the on-off valve has a valving element operated by pressure inside the operation tube to open and close an opening end communicating the inlet tube with the voice assist tube (Patent Document 1: JP 2009-153775 A).

According to the voice assist apparatus of Patent Document 1, inspiration gas is supplied from the gas feeder to the trachea of a patient through the respiratory tube and filled in the lungs of a patient to pressurize the inside of the respiratory tube, during expiration. When the inside of the respiratory tube is pressurized, the pressure inside the operation tube communicating with the respiratory tube increases to operate the valving element of the on-off valve and close the open end communicating the inlet tube with the voice assist tube.

On the other hand, when the inside of the respiratory tube is depressurized to approximate atmospheric pressure during expiration of a patient, the pressure inside the operation tube communicating with the respiratory tube decreases. When the pressure inside the operation tube decreases, the valving element of the on-off valve connected with the operation tube is operated to open the open end communicating the inlet tube with the voice assist tube.

Then, voice assist gas that has been supplied from the inlet tube is introduced to the voice assist tube and the trachea of a patient to flow to and vibrate the vocal chords of a patient for vocalization.

As mentioned above, in the voice assist apparatus of Patent Document 1, the operation tube closes the on-off valve when the inside of the respiratory tube is pressurized during expiration of a patient. On the other hand, the operation tube opens the on-off valve when the pressure inside of the respiratory tube is decreased by communicating with atmosphere during inspiration of a patient. Then, voice assist gas is supplied to the trachea of a patient to vibrate the vocal chords of a patient for vocalization.

Therefore, the patients do not need complex operation at every expiration but can vocalize during expiration and have a conversation in a near-natural voice.

SUMMARY

However, in the voice assist apparatus of Patent Document 1, the valving element of the on-off valve opening and closing the open end communicating the inlet tube with the voice assist tube is operated by increasing and decreasing the pressure inside the operation tube. When the pressure inside the operation tube relatively slightly increases and decreases, the valving element of the on-off valve may not be correctly operated so that the patients cannot have a conversation in a near-natural voice.

An objective of the present invention is to provide a voice assist apparatus capable of vocalization in a near-natural voice by correctly flowing and blocking voice assist gas during expiration and inspiration, respectively, of a patient even when the pressure inside the operation tube relatively slightly increases and decreases.

(1) A voice assist apparatus used with an artificial respiratory device provided with:

an inspiration gas-inlet tube with a first end being connected with a supply source of inspiration gas, an endotracheal tube endotracheally inserted from a trachea incision that a patient has, and an on-off valve, the on-off valve being connected with the inspiration gas-inlet tube and a first end of the endotracheal tube, the on-off valve being opened up to and closed off from atmosphere at the timings of expiration and inspiration, respectively, of a patient, includes:

a voice assist gas-inlet tube with a first end being connected with a supply source of voice assist gas;

a voice assist tube with a first end being endotracheally inserted from the trachea incision of a patient;

an operation tube with a first end being connected with the on-off valve to communicate with the endotracheal tube; and a main body connected with respective second ends of the voice assist gas-inlet tube, the voice assist tube, and the operation tube, in which the main body has:

a first chamber connected with the second end of the voice assist gas-inlet tube, a second chamber connected with the second end of the voice assist tube, a third chamber connected with the second end of the operation tube, a dividing wall dividing between the first chamber and the second chamber except an opening communicating the first chamber with the second chamber, and a membrane formed elastically deformably to open and close the opening, the membrane isolating the third chamber from the first chamber and the second chamber.

According to the constitution of (1), the voice assist apparatus is used with an artificial respiratory device provided with an inspiration gas-inlet tube, an endotracheal tube, and an on-off valve, the on-off valve being connected with the inspiration gas-inlet tube and a first end of the endotracheal tube, the on-off valve being opened up to and closed off from atmosphere at the timings of expiration and inspiration, respectively, of a patient.

The voice assist apparatus is provided with a voice assist gas-inlet tube, a voice assist tube, an operation tube, and a main body.

The voice assist gas-inlet tube has a first end connected with a supply source of voice assist gas.

The voice assist tube has a first end endotracheally inserted from the trachea incision of a patient.

The operation tube has a first end connected with the on-off valve to communicate with the endotracheal tube.

The main body is connected with respective second ends of the voice assist gas-inlet tube, the voice assist tube, and the operation tube.

The main body has a first chamber, a second chamber, a third chamber, a dividing wall, and a membrane.

The first chamber is connected with the second end of the voice assist gas-inlet tube.

The second chamber is connected with the second end of the voice assist tube.

The third chamber is connected with the second end of the operation tube.

The dividing wall divides between the first chamber and the second chamber except an opening communicating the first chamber with the second chamber.

The membrane is formed elastically deformably to open and close the opening and isolates the third chamber from the first chamber and the second chamber.

Accordingly, the artificial respiratory device is opened up to and closed off from atmosphere at the timings of expiration and inspiration, respectively, of a patient. As a result, the pressure inside the endotracheal tube in the artificial respiratory device decreases and increases at the timings of expiration and inspiration, respectively, of a patient.

In the voice assist apparatus used with such an artificial respiratory device, the pressures inside the operation tube communicating with the endotracheal tube and inside the third chamber connected with the operation tube are decreased at the timing of expiration of a patient. As a result, the elastically deformable membrane expands away from the dividing wall to open the opening. In this case, voice assist gas flows from the voice assist gas-inlet tube to the first chamber, the opening, the second chamber, the voice assist tube, and then the trachea of a patient to vibrate the vocal chords of a patient for vocalization.

On the other hand, in the voice assist apparatus, the pressures inside the operation tube communicating with the endotracheal tube and inside the third chamber connected with the operation tube are increased at the timing of inspiration of a patient. As a result, the elastically deformable membrane expands close to the dividing wall to close the opening. In this case, voice assist gas flows from the voice assist gas-inlet tube to the first chamber but is blocked by the membrane. Therefore, the voice assist gas cannot not flow to the second chamber, the voice assist tube, or the trachea of a patient so that the vocal chords of a patient cannot be vibrated for vocalization.

Thus, not a structure such as a valving element but the membrane can correctly flow and block voice assist gas during expiration and inspiration, respectively, of a patient by switching the directions in which the membrane expands even when the pressure inside the endotracheal tube relatively slightly increases and decreases.

Therefore, the present invention can provides a voice assist apparatus capable of vocalization in a near-natural voice by correctly flowing and blocking voice assist gas during expiration and inspiration, respectively, of a patient even when the pressure inside the operation tube relatively slightly increases and decreases.

(2) In the voice assist apparatus according to (1), the dividing wall has an edge being in contact with the membrane when the membrane closes the opening, and the main body has an additional wall having an additional edge bearing a symmetrical relationship to the edge with respect to the center of the membrane.

According to the constitution of (2), the dividing wall has an edge being in contact with the membrane when the membrane closes the opening.

Furthermore, the main body has an additional wall having an additional edge bearing a symmetrical relationship to the edge with respect to the center of the membrane.

Accordingly, the membrane expands to be brought into contact with the edge of the dividing wall as well as the additional edge bearing a symmetrical relationship to the edge with respect to the center of the membrane so as to close the opening. This balances the expansion of the membrane when the membrane is in contact with the edge of the dividing wall so as to firmly close the opening.

Therefore, the present invention can correctly flow and block voice assist gas during expiration and inspiration, respectively, of a patient even when the pressure inside the operation tube relatively slightly increases and decreases so as to provide a voice assist apparatus capable of vocalization in a near-natural voice.

The present invention can provides a voice assist apparatus capable of vocalization in a near-natural voice by correctly flowing and blocking voice assist gas during expiration and inspiration, respectively, of a patient even when the pressure inside the operation tube relatively slightly increases and decreases.

DETAILED DESCRIPTION

The configuration of the voice assist apparatus 40 according to an embodiment of the present invention is explained below by reference to the attached drawings.

Figure 1:
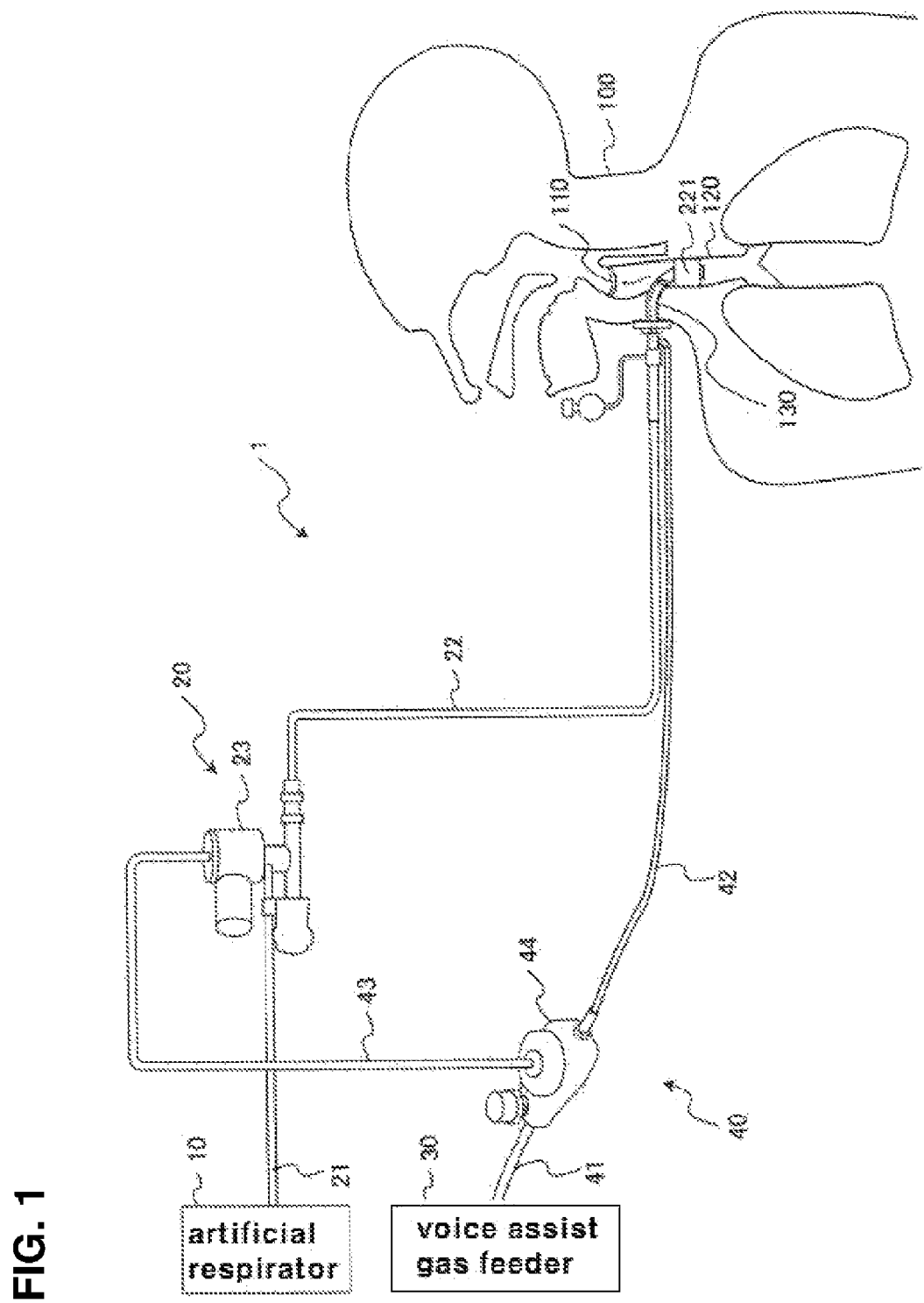
FIG. 1 shows the overall schematic view illustrating an artificial respirator-coupled voice assist apparatus 1 formed by using the voice assist apparatus 40 according to an embodiment of the present invention.

FIG. 1 shows the overall schematic view illustrating an artificial respirator-coupled voice assist apparatus 1 formed by using the voice assist apparatus 40 according to an embodiment of the present invention.

The voice assist apparatus 40 is used with an artificial respiratory device 20. Specifically, the voice assist apparatus 40 is used in the artificial respirator-coupled voice assist apparatus 1.

The artificial respirator-coupled voice assist apparatus 1 is used for a patient 100 who has an incision in the trachea 120 of a patient 100 under the vocal chords 110 of a patient 100 and breathes with an artificial respiratory device 20 through this trachea incision 130. The artificial respirator-coupled voice assist apparatus 1 reproduces the natural voice of a patient 100 by flowing gas to artificially vibrate the vocal chords 110 of a patient 100 with the voice assist apparatus 40.

The artificial respirator-coupled voice assist apparatus 1 is provided with an artificial respirator 10 as the supply source of inspiration gas, an artificial respiratory device 20, a voice assist gas feeder 30 as the supply source of voice assist gas, and a voice assist apparatus 40.

The artificial respirator 10 supplies a predetermined volume of inspiration gas (air, oxygen, or the like) necessary for a single breath of a patient 100 to the artificial respiratory device 20 over a predetermined time by controlling a controller provided with a CPU, a memory, etc.

The artificial respiratory device 20 is provided with an inspiration gas-inlet tube 21, an endotracheal tube 22, and an on-off valve 23.

The inspiration gas-inlet tube 21 has a first end connected with the artificial respirator 10 and a second end connected with the on-off valve 23.

The endotracheal tube 22 has a first end inserted from the trachea incision 130 to the trachea 120 of a patient 100 and a second end connected with the on-off valve 23. A cuff 221 preventing gas exhausted from the lungs of a patient 100 from flowing out to the mouth of a patient 100 is installed in the first end side of the endotracheal tube 22 inside the trachea 120 of a patient 100.

The on-off valve 23 is connected with the inspiration gas 21 and the second end of the endotracheal tube 22. The on-off valve 23 is opened up to and closed off from atmosphere at the timings of expiration and inspiration, respectively, of a patient 100 by controlling the artificial respirator 10. As a result, the pressure inside the artificial respiratory device 20 decreases and increases at the timings of expiration and inspiration, respectively, of a patient 100.

The on-off valve 23 may be an air valve opened and closed by supplying inspiration gas through the control of the artificial respirator 10. Alternatively, the on-off valve 23 may be a solenoid valve opened and closed by an electric signal through the control of the artificial respirator 10.

The voice assist gas feeder 30 supplies voice assist gas to the voice assist apparatus 40.

The voice assist gas feeder 30 may have any structure as long as supplying voice assist gas. For example, the voice assist gas feeder 30 may form an air pump capable of supplying air etc.

The voice assist apparatus 40 is provided with a voice assist gas-inlet tube 41, a voice assist tube 42, an operation tube 43, and a main body 44.

The voice assist gas-inlet tube 41 has a first end connected with the voice assist gas feeder 30 and a second end connected with the main body 44.

The voice assist tube 42 has a first end inserted from the trachea incision 130 to the trachea 120 of a patient 100 and a second end connected with the main body 44.

The operation tube 43 has a first end connected with the on-off valve 23 to communicate with the endotracheal tube 22 and a second end connected with the main body 44.

The main body 44 is connected with respective second ends of the voice assist gas-inlet tube 41, the voice assist tube 42, and the operation tube 43.

Figure 2:
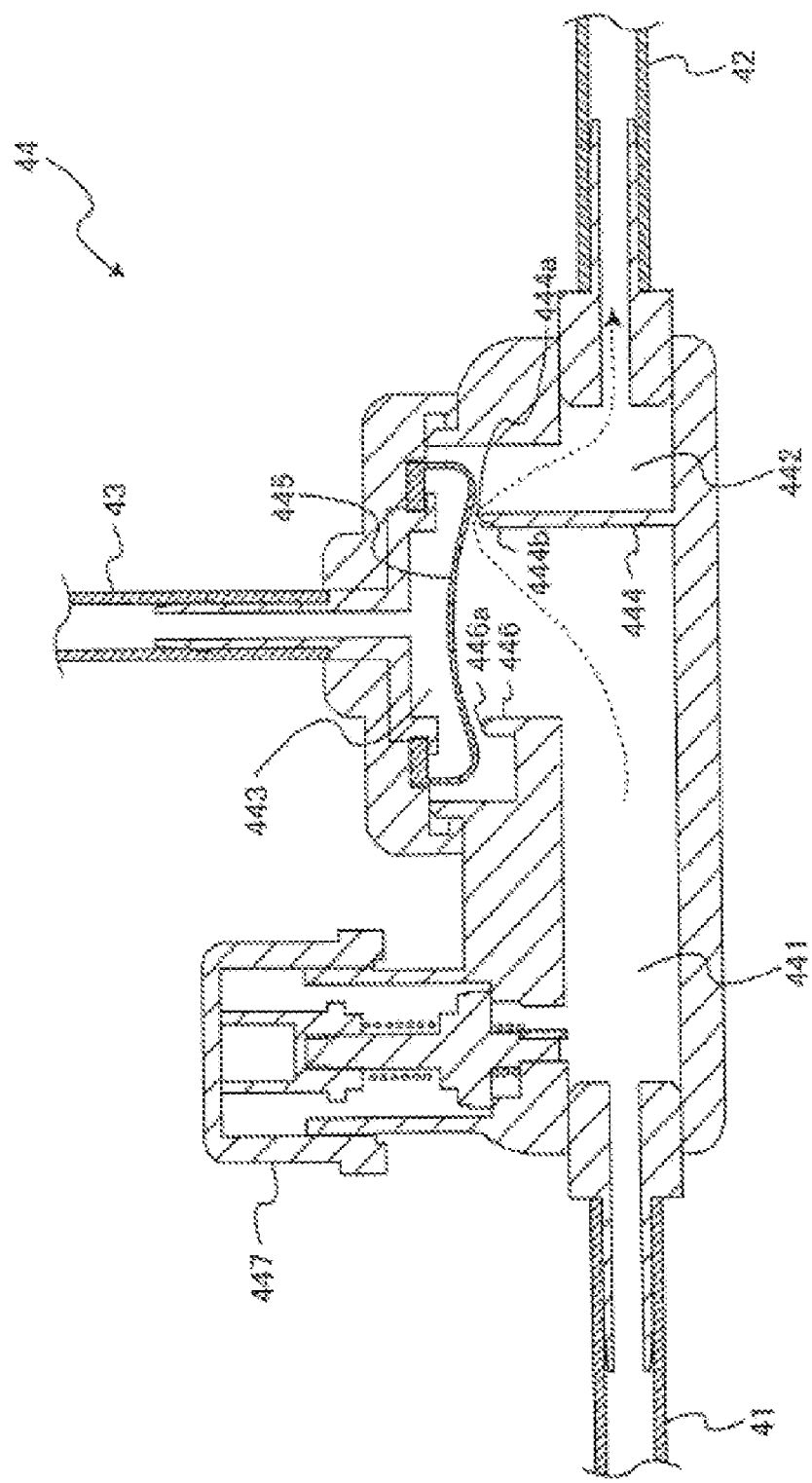
FIG. 2 shows the cross-sectional view of the main body 44 according to the embodiment.

FIG. 2 shows the cross-sectional view of the main body 44 according to the embodiment.

The main body 44 has a first chamber 441, a second chamber 442, a third chamber 443, a dividing wall 444, a membrane 445, an additional wall 446, and a relief valve 447.

The first chamber 441 is connected with the second end of the voice assist gas-inlet tube 41.

The second chamber 442 is connected with the second end of the voice assist tube 42.

The third chamber 443 is connected with the second end of the operation tube 43.

The dividing wall 444 divides between the first chamber 441 and the second chamber 442 except an opening 444a communicating the first chamber 441 with the second chamber 442.

The dividing wall 444 has an edge 444b being in contact with the membrane 445 when the membrane 445 closes the opening 444a.

The membrane 445 is formed from an elastically deformable member (e.g. rubber member) to open and close the opening and isolates the third chamber 443 from the first chamber 441 and the second chamber 442.

The membrane 445 expands away from the dividing wall 444 dividing between the first chamber 441 and the second chamber 442 and then from the edge 444b to open the opening 444a when the pressure inside the third chamber 443, i.e. the pressures inside the operation tube 43 communicating with the third chamber 443 and inside the endotracheal tube 22 (see FIG. 1) communicating with the operation tube 43 decrease, as shown in FIG. 2.

Figure 3:
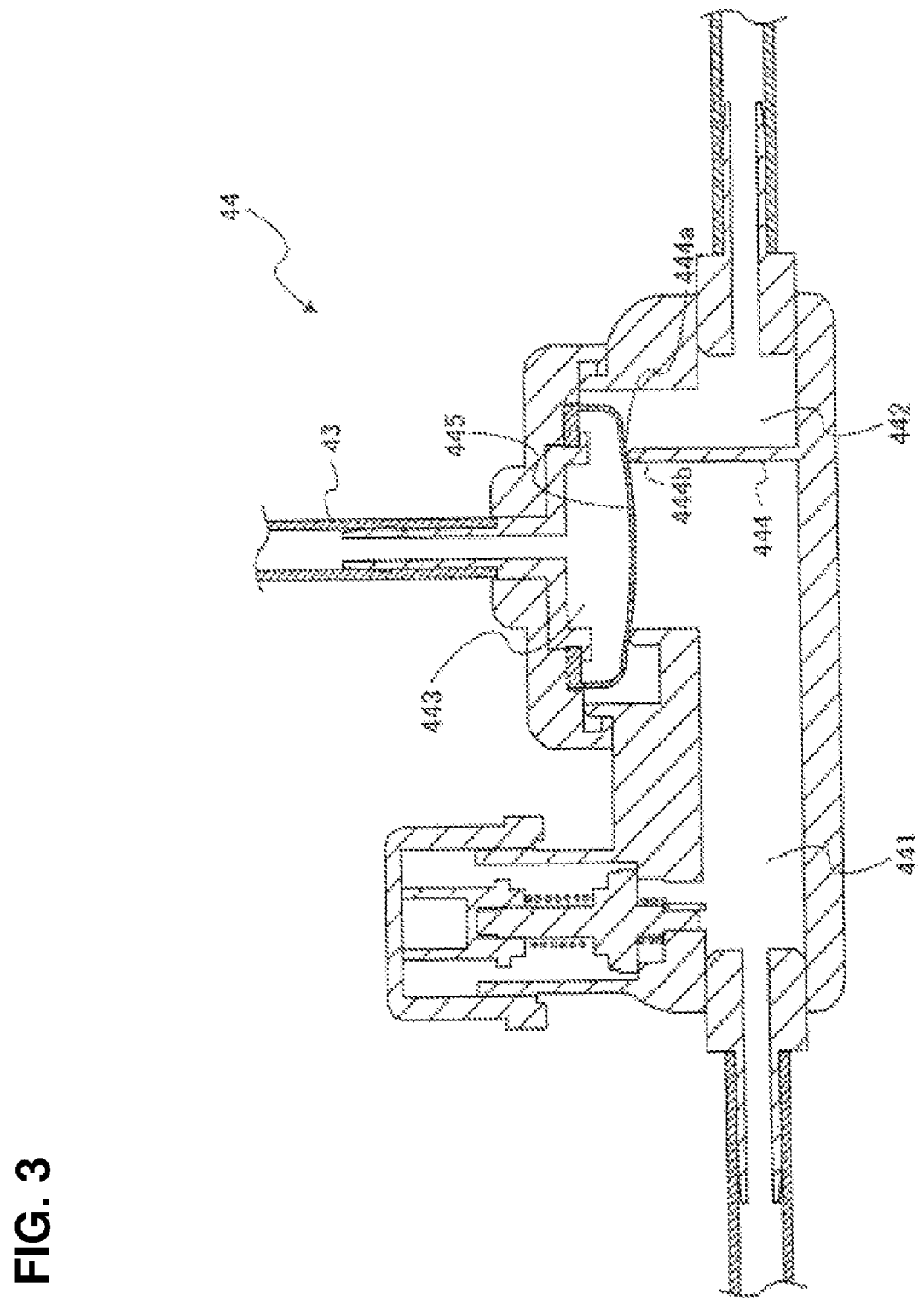
FIG. 3 shows the cross-sectional view of the main body 44 according to the embodiment.

FIG. 3 shows the cross-sectional view of the main body 44 according to the embodiment. FIG. 3 shows that the membrane 445 is in contact with the edge 444b of the dividing wall 444 when the opening 444a is closed.

The membrane 445 expands toward the dividing wall 444 dividing between the first chamber 441 and the second chamber 442 and is brought into contact with the edge 444b to close the opening 444a when the pressure inside the third chamber 443, i.e. the pressures inside the operation tube 43 communicating with the third chamber 443 and inside the endotracheal tube 22 (see FIG. 1) communicating with the operation tube 43 increase, as shown in FIG. 3.

Returning to FIG. 2, the additional wall 446 has an additional edge 446a bearing a symmetrical relationship to the edge 444b of the dividing wall 444 with respect to the center of the membrane 445.

The relief valve 447 is a movable valve closing the first chamber 441 off from atmosphere. When the pressure inside the first chamber 441 is a predetermined value or more (but the membrane 445 is not elastically deformed), the movable valve is operated to communicate the first chamber 441 with atmosphere.

According to the above-mentioned configuration, voice assist gas supplied from the voice assist gas feeder 30 (see FIG. 1) flows in the first chamber 441 through the voice assist gas-inlet tube 41.

The voice assist gas that has been flowed in the first chamber 441 flows in the opening 444a, the second chamber 442, the voice assist tube 42, and then the trachea 120 of a patient 100 (see FIG. 1) to vibrate the vocal chords 110 of a patient (see FIG. 1) when the membrane 445 expands away from the dividing wall 444 to open the opening 444a.

On the other hand, the voice assist gas that has been flowed in the first chamber 441 does not flow in the second chamber 442 when the membrane 445 expands toward the dividing wall 444 to close the opening 444a. The voice assist gas that has been flowed in the first chamber 441 flows outside the main body 44 through the relief valve 447 when the pressure inside the first chamber 441 is a predetermined value or more.

The functioning of the artificial respirator-coupled voice assist apparatus 1 is explained below.

In the artificial respiratory device 20, the on-off valve 23 is opened up to and closed off from atmosphere at the timings of expiration and inspiration, respectively, of a patient 100 by controlling the artificial respirator 10. As a result, the pressure inside the endotracheal tube 22 in the artificial respiratory device decreases and increases at the timings of expiration and inspiration, respectively, of a patient 100.

In the voice assist apparatus 40, the pressures inside the operation tube 43 communicating with the endotracheal tube 22 and inside the third chamber 443 connected with the operation tube 43 are decreased at the timing of expiration of a patient 100. As a result, the elastically deformable membrane 445 expands away from the dividing wall 444 to open the opening 444a, as shown in FIG. 2. In this case, voice assist gas flows from the voice assist gas feeder 30 to the voice assist gas-inlet tube 41, the first chamber 441, the opening 444a, the second chamber 442, the voice assist tube 42, and then the trachea 120 of a patient 100 to vibrate the vocal chords 110 of a patient 100 for vocalization.

On the other hand, in the voice assist apparatus 40, the pressures inside the operation tube 43 communicating with the endotracheal tube 22 and inside the third chamber 443 connected with the operation tube 43 are increased at the timing of inspiration of a patient 100. As a result, the elastically deformable membrane 445 expands close to the dividing wall 444 to close the opening 444a, as shown in FIG. 3. In this case, voice assist gas flows from the voice assist gas feeder 30 to the voice assist gas-inlet tube 41 and the first chamber 441 but is blocked by the membrane 445. Therefore, the voice assist gas does not flow to the second chamber 442, the voice assist tube 42, or the trachea 120 of a patient 100 so that the vocal chords 110 of a patient 100 cannot be vibrated for vocalization.

According to the voice assist apparatus 40 of the embodiment, not a structure such as a valving element but the membrane 445 can correctly flow and block voice assist gas during expiration and inspiration, respectively, of a patient by switching the directions in which the membrane expands even when the pressure inside the endotracheal tube 22 relatively slightly increases and decreases.

Therefore, the present invention can provides a voice assist apparatus capable of vocalization in a near-natural voice by correctly flowing and blocking voice assist gas during expiration and inspiration, respectively, of a patient even when the pressure inside the operation tube relatively slightly increases and decreases.

According to the voice assist apparatus 40 of the embodiment, the membrane 445 expands to be brought into contact with the edge 444b of the dividing wall 444 as well as the additional edge 446a bearing a symmetrical relationship to the edge 444b with respect to the center of the membrane 445 so as to close the opening 444a. This balances the expansion of the membrane 445 when the membrane 445 is in contact with the edge 444b of the dividing wall 444 so as to firmly close the opening 444a.

Therefore, the present invention can correctly flow and block voice assist gas during expiration and inspiration, respectively, of a patient even when the pressure inside the operation tube relatively slightly increases and decreases so as to provide a voice assist apparatus capable of vocalization in a near-natural voice.

The present invention is not limited to the above-mentioned embodiment but embraces variations, modifications, etc. without departing from the scope of the present invention.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

REFERENCE SIGNS LIST 1 artificial respirator-coupled voice assist apparatus
10 artificial respirator
20 artificial respiratory device
21 inspiration gas-inlet tube
22 endotracheal tube
23 on-off valve
30 voice assist gas feeder
40 voice assist apparatus
41 voice assist gas-inlet tube
42 voice assist tube
43 operation tube
44 main body
100 patient
110 vocal chords
120 trachea
130 trachea incision
221 cuff
441 first chamber
442 second chamber
443 third chamber
444 dividing wall
444a opening
444b edge
445 membrane
446 additional wall
446a additional edge
447 relief valve

What is claimed is:

1. A voice assist apparatus used with an artificial respiratory device provided with:
   an inspiration gas-inlet tube with a first end being connected with a supply source of inspiration gas,
   an endotracheal tube adapted to be endotracheally connected to a trachea incision that a patient has, and
   an on-off valve, the on-off valve being connected with the inspiration gas-inlet tube and a first end of the endotracheal tube, the on-off valve being opened up to and closed off from atmosphere at timings of expiration and inspiration, respectively, of a patient,
   the voice assist apparatus comprising:
   a voice assist gas-inlet tube with a first end being connected with a supply source of voice assist gas;
   a voice assist tube with a first end being inserted into the trachea incision of a patient;
   an operation tube with a first end being connected with the on-off valve to communicate with the endotracheal tube; and
   a main body connected with respective second ends of the voice assist gas-inlet tube, the voice assist tube, and the operation tube, wherein the main body has:
- a first chamber connected with the second end of the voice assist gas-inlet tube,
- a second chamber connected with the second end of the voice assist tube,
- a third chamber connected with the second end of the operation tube,
- a dividing wall dividing between the first chamber and the second chamber except an opening communicating the first chamber with the second chamber, and
- a membrane elastically deformable to open and close the opening, wherein the membrane isolates the third chamber from the first chamber and the second chamber.

2. The voice assist apparatus according to claim 1, wherein the dividing wall has an edge being in contact with the membrane when the membrane closes the opening, and
the main body has an additional wall having an additional edge bearing a symmetrical relationship to the edge with respect to the center of the membrane.

* * * * *